United States Patent [19]

Kuroda et al.

[11] Patent Number: 5,158,848
[45] Date of Patent: Oct. 27, 1992

[54] PHOTOCONDUCTOR FOR ELECTROPHOTOGRAPHY

[75] Inventors: Masami Kuroda; Yoshinobu Sugata; Noboru Furusho, all of Kawasaki, Japan

[73] Assignee: Fuji Electric Co., Ltd., Kawasaki, Japan

[21] Appl. No.: 641,730

[22] Filed: Jan. 15, 1991

[30] Foreign Application Priority Data

Jan. 17, 1990 [JP] Japan .................................. 2-8026
Mar. 26, 1990 [JP] Japan ................................ 2-76213

[51] Int. Cl.$^5$ ........................................ G03G 5/047
[52] U.S. Cl. ................................. 430/59; 430/58; 430/75; 430/77; 430/83; 430/78
[58] Field of Search ................ 430/58, 59, 75, 76, 430/78, 77, 83

[56] References Cited

U.S. PATENT DOCUMENTS

| 3,189,447 | 6/1965 | Neugebauer et al. | 96/1 |
| 3,484,237 | 12/1969 | Shattuck et al. | 96/1.5 |
| 4,150,987 | 4/1979 | Anderson et al. | 96/1.5 R |
| 4,278,747 | 7/1981 | Murayama et al. | 430/82 |
| 4,353,971 | 10/1982 | Chang et al. | 430/58 |
| 4,367,273 | 1/1983 | Murayama et al. | 430/56 |
| 4,385,106 | 5/1983 | Sakai | 420/59 |
| 4,415,640 | 11/1983 | Goto et al. | 430/59 |
| 4,448,868 | 5/1985 | Suzuki et al. | 430/58 |
| 4,565,761 | 1/1986 | Katagiri et al. | 430/83 |
| 4,568,623 | 2/1986 | Makino et al. | 430/58 |
| 4,606,986 | 8/1986 | Yanus et al. | 430/59 |
| 4,624,904 | 11/1986 | Kazmaier et al. | 430/59 |
| 4,629,670 | 12/1986 | Katagiri et al. | 430/58 |
| 4,629,672 | 12/1986 | Makino et al. | 430/76 |
| 4,666,809 | 5/1987 | Matsumoto et al. | 430/76 |
| 4,673,630 | 6/1987 | Katagiri et al. | 430/72 |
| 4,677,045 | 6/1987 | Champ et al. | 430/59 |
| 4,702,983 | 10/1987 | Haino et al. | 430/75 |
| 4,731,315 | 3/1988 | Horie et al. | 430/77 |
| 4,783,387 | 11/1988 | Ueda | 430/76 |
| 4,808,503 | 2/1989 | Yamada et al. | 430/75 |
| 4,839,252 | 6/1989 | Murata et al. | 430/59 |
| 4,861,691 | 8/1989 | Kuroda et al. | 430/59 |
| 4,861,692 | 8/1989 | Kuroda et al. | 430/59 |
| 4,865,934 | 9/1989 | Ueda et al. | 430/59 |
| 4,871,636 | 10/1989 | Hattori et al. | 430/77 |
| 4,877,703 | 10/1989 | Kuroda et al. | 430/76 |
| 4,882,255 | 11/1989 | Hattori et al. | 430/73 |

(List continued on next page.)

FOREIGN PATENT DOCUMENTS 0034942 9/1981 European Pat. Off. .
0131140 1/1985 European Pat. Off. .
0270685 6/1988 European Pat. Off. .

(List continued on next page.)

Primary Examiner—Marion E. McCamish
Assistant Examiner—Rosemary Ashton
Attorney, Agent, or Firm—Spencer, Frank & Schneider

[57] ABSTRACT

A photoconductor for electrophotography comprises a substrate and a photosensitive layer formed thereon and including a novel hydrazone compound as a charge transporting substance. The hydrazone compound is represented by the following general formula:

Wherein, A is selected from the residual group consisting of an aromatic residual group, a condensed polycyclic residual group, and a heterocyclic residual group, which groups may be or not may be substituted, $R_1$ is selected from the atom or group consisting of any one of a hydrogen atom, a halogen atom, an alkyl group, an acyl group or a dialkylamino group, and each of $R_2$ and $R_3$ is selected from the group consisting of an alkyl group, an aryl group, an alkenyl group, an aralkyl group and a thenyl group, which groups may be or not may be substituted.

5 Claims, 1 Drawing Sheet

U.S. PATENT DOCUMENTS

| | | |
|---|---|---|
| 4,910,110 | 3/1990 | Kuroda et al. ......... 430/59 |
| 4,929,525 | 5/1990 | Kuroda et al. ......... 430/75 |
| 4,935,323 | 6/1990 | Hattori et al. ......... 430/58 |
| 4,945,021 | 7/1990 | Takata et al. ......... 430/76 |
| 4,948,689 | 8/1990 | Kuroda et al. ......... 430/59 |
| 4,950,572 | 8/1990 | Kuroda et al. ......... 430/59 |
| 4,954,405 | 9/1990 | Sugata et al. ......... 430/58 |
| 4,956,250 | 9/1990 | Kuroda et al. ......... 430/58 |
| 4,956,255 | 9/1990 | Ueda ......... 430/59 |
| 4,956,277 | 9/1990 | Kuroda et al. ......... 430/58 |
| 4,957,837 | 9/1990 | Kuroda et al. ......... 430/59 |
| 4,971,876 | 11/1990 | Kuroda et al. ......... 430/75 |
| 4,985,325 | 1/1991 | Kuroda et al. ......... 430/59 |
| 4,988,594 | 1/1991 | Hattori et al. ......... 430/59 |

FOREIGN PATENT DOCUMENTS

| | | |
|---|---|---|
| 37543 | 6/1959 | Fed. Rep. of Germany . |
| 2041490 | 3/1971 | Fed. Rep. of Germany . |
| 3019909 | 11/1980 | Fed. Rep. of Germany . |
| 3141306 | 6/1982 | Fed. Rep. of Germany . |
| 3139524 | 8/1982 | Fed. Rep. of Germany . |
| 3203621 | 9/1982 | Fed. Rep. of Germany . |
| 3208337 | 9/1982 | Fed. Rep. of Germany . |
| 3303830 | 8/1983 | Fed. Rep. of Germany . |
| 3320674 | 12/1983 | Fed. Rep. of Germany . |
| 3643341 | 6/1987 | Fed. Rep. of Germany . |
| 3842253 | 6/1989 | Fed. Rep. of Germany . |
| 54-150128 | 11/1979 | Japan . |
| 1100558 | 4/1980 | Japan . |
| 55-42380 | 10/1980 | Japan . |
| 116039 | 9/1981 | Japan . |
| 118846 | 9/1981 | Japan . |
| 57-101844 | 6/1982 | Japan . |
| 176055 | 10/1982 | Japan . |
| 198043 | 11/1983 | Japan . |
| 59-2023 | 1/1984 | Japan . |
| 50445 | 3/1984 | Japan . |
| 133553 | 7/1984 | Japan . |
| 182456 | 10/1984 | Japan . |
| 182457 | 10/1984 | Japan . |
| 204840 | 11/1984 | Japan . |
| 5941 | 2/1985 | Japan . |
| 93443 | 5/1985 | Japan . |
| 45664 | 10/1985 | Japan . |
| 60-052 | 12/1985 | Japan . |
| 29496 | 7/1986 | Japan . |
| 262052 | 11/1987 | Japan . |
| 264055 | 11/1987 | Japan . |
| 131146 | 6/1988 | Japan . |
| 158560 | 7/1988 | Japan . |
| 189870 | 8/1988 | Japan . |
| 189871 | 8/1988 | Japan . |
| 208849 | 8/1988 | Japan . |
| 63-244043 | 10/1988 | Japan . |
| 567 | 1/1989 | Japan . |
| 49050 | 2/1989 | Japan . |
| 185637 | 7/1989 | Japan . |
| 234856 | 9/1989 | Japan . |
| 241561 | 9/1989 | Japan . |
| 79855 | 3/1990 | Japan . |
| 284659 | 3/1990 | Japan . |

F I G . 1

F I G . 2

F I G . 3

PHOTOCONDUCTOR FOR ELECTROPHOTOGRAPHY

BACKGROUND OF THE INVENTION

1. Field of the Invention

The present invention relates to photoconductors for electrophotography, and particularly to a photoconductor for electrophotography which contains a novel hydrazone compound in the photosensitive layer thereof formed on an electroconductive substrate.

2. Description of the Prior Art

Photosensitive materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and bisazo compounds, dispersions of such organic polymeric photoconductive substances in resin binders, and vacuum evaporated organic polymeric photoconductive substances.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the transportation of electric charge upon receiving light. In an electrophotographic method using a photoconductor of the kind as mentioned above, for example, the Carlson's system is applied to image formation. The image formation according to this system comprises steps of subjecting a photoconductor in the dark to corona discharge to charge the photoconductor, illuminating the surface of the charge photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralization of the residual charge with light (erasion), and so on to be ready for reuse.

Photoconductors for electrophotography in which use is made of an organic materials have recently been put into practical use by virtue of the advantageous features of the organic materials such as flexibility, thermal stability, and/or a film forming capacity. Various charge transporting materials are known, for instance, oxadiazol compounds (disclosed in U.S. Pat. No. 3,189,447), pirazoline compounds in Japanese Patent Application Publication No. 2023/1984 and hydrazone compounds in Japanese Patent Application Publication No. 42,380/1980, Japanese Patent Application Laying-open No. 101,844/1982, and Japanese Patent Application Laying-open No. 150,128/1979 and so on.

Although organic materials have a number of advantageous features mentioned above with which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography to be used in copying apparatuses and printers which photoconductor has a high photosensitivity and excellent characteristics in repeated use, through the use, in the photosensitive layer, of a novel organic materials not used to date as a charge transporting substance.

In the aspect of the present invention, a photoconductor for electrography comprises:
  a substrate; and
  a photosensitive layer formed on the substrate and containing a charge generating substance and at least one of hydrazone compounds represented by the following general formula (I), (II) or (III) as a charge transporting substance;

wherein, A is a residual group selected from the group consisting of an aromatic residual group, a condensed polycyclic aromatic residual group, and a heterocyclic residual group, which groups may be or not may be substituted, $R_1$ is selected from the group or atom consisting of a hydrogen atom, a halogen atom, an alkyl group, an acyl group and a dialkylamino group, and each of $R_2$ and $R_3$ is a group selected from the group consisting of an alkyl group, an aryl group, an alkenyl group, an aralkyl group and a thenyl group, which groups may be or not may be substituted, wherein, each of A, $R_2$ and $R_3$ is the same group as that of the general formula (I), wherein, R4 is selected from the atom or group consisting of a hydrogen atom, a halogen atom and an alkyl group, each of $R_2$ and $R_3$ is the same group as that of the general formula (I), and n is an integer of 1 or 2.

Here, the photosensitive layer may comprise a layer including a dispersion of a charge generating substance and a charge transporting substance selected from at least one of hydrazone compounds represented by the general formula (I), (II) or (III) in a binder resin.

The photosensitive layer may comprise a laminate of a charge transporting layer including a charge transporting substance selected from at least one of hydrazone compounds represented by the general formula (I), (II) or (III) and a charge generating layer.

DETAILED DESCRIPTION OF PREFERRED EMBODIMENTS

A photoconductor according to the present invention contains a specific hydrazone compound as explained later in the photosensitive layer as a charge transporting substance. The photoconductor may be in the form of any one of the structures of FIGS. 1, 2 and 3, depending on the way of application of the hydrazone compound thereto.

Figure 1:
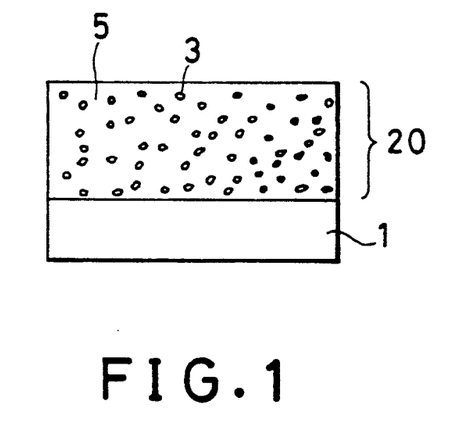
FIGS. 1 to 3 are schematic cross-sectional views of photoconductors according to the present invention, respectively.
Figure 2:
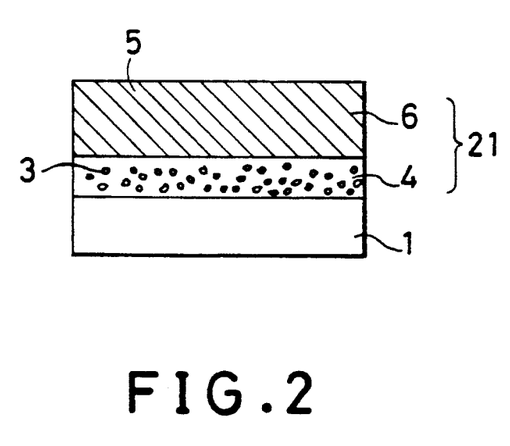
Figure 3:
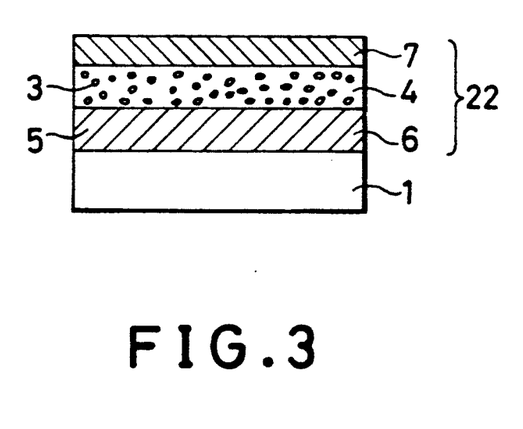

FIGS. 1, 2 and 3 are schematic cross-sectional views of different embodiments of the photoconductor of the present invention, respectively.

FIG. 1 shows a monolayer type photoconductor. A photosensitive layer 20 is provided on an electroconductive substrate 1. The photosensitive layer 20 comprises a charge generating substance 3 and a specific hydrazone compound as a charge transporting substance 5 both of which substances are dispersed in a resin binder matrix so that the photosensitive layer 20 functions as photoconductor.

FIG. 2 shows a laminate type photoconductor. A laminated photosensitive layer 21 is provided on an electroconductive substrate 1, a lower layer of the laminate is a charge generating layer 4 including a charge generating substance 3 as a main component and an upper one is a charge transporting layer 6 containing a specific hydrazone compound as a charge transporting substance 5, so that the photosensitive layer 21 functions as a photoconductor. A covering layer 7 can be generally provided as shown in FIG. 3 if necessary.

FIG. 3 shows another laminate type photoconductor having a photosensitive layer 22 of the structure in reverse to that of FIG. 2. A laminated photosensitive layer 2C is provided on an electroconductive substrate 1, a lower layer of the laminate is a charge transporting layer 6 including a specific hydrazone compound as a charge transporting substance 5 and an upper one is a charge generating layer 4 including a charge generating substance 3. The photosensitive layer also functions as a photoconductor. This photoconductor is usually used according to the positive charge mode. In this case, a covering layer 7 may generally be further provided as shown in FIG. 3 to protect the charge generating layer 4.

Thus, there are two different types of layer structures in the photoconductor. The reason for this is that, even if any photoconductor with the layer structure as shown in FIG. 2 is to be used in the positive charge mode, no charge transporting substances adaptable to the positive charge mode have been found yet. Accordingly, when the positive charge mode is adapted, the photoconductor is required of a layer structure as shown in FIG. 3 at present.

A photoconductor as shown in FIG. 1 can be produced by dispersing a charge generating substance in a solution of a specific hydrazone compound as a charge transporting substance and a resin hinder and applying the resulting dispersion on an electroconductive substrate.

A photoconductor as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a specific hydrazone compound as a charge transporting substance and a resin binder on the resulting layer and drying.

A photoconductor as shown in FIG. 3 can be prepared by applying and drying a solution of a specific hydrazone compound as a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the coating layer, followed by formation of a covering layer.

The electroconductive substrate 1 serves as an electrode of the photoconductor and as a support for a layer or layers formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a particulate charge generating substance 3 in a resin binder or by deposition of a charge generating substance by means of vacuum evaporation, or the like technique as described above, and this layer generates an electric charge upon receiving light. It is important that the charge generating layer 4 be high not only in charge generating efficiency but also in capability of injecting the generated electric charge into the charge transporting layer 6 and any covering layer 7, whose capability is desirably as little dependent upon the electric field as possible and high even in low intensity electric fields.

Usable charge generating substances include metal-free phthalocyanine, phthalocyanine compounds such as titanyl phthalocyanine; various azo, quinone and indigo pigments; dyes such a cyanine, squarylium, azulenium, and pyrylium compounds; and selenium and selenium compounds. Among them, a suitable compound can be chosen depending on the wavelength range of a light source used for the image formation. The thickness of the charge generating layer is determined depending on the extinction coefficient of a charge generating substance to be used therein in view of the layer's function of generating an electric charge, but is generally 5 $\mu$m or smaller, preferably 1 $\mu$m or smaller. It also is possible to form a charge generating layer using a charge generating substance as a main component in mixture with a charge transporting substance and so on.

Resin binders include polycarbonates, polyesters, polyamides, polyurethanes, vinyl chloride resins, epoxy resins, diallylphtalate resins, silicone resins, and methacrylate ester homopolymer and copolymers, which may be used either alone or in an appropriate composition ratio.

The charge transporting layer 6 is a coating film containing a specific hydrazone compound, which will be described later in detail, as an organic charge transporting substance in a resin binder. The charge transporting layer serves as an insulator layer in the dark so as to retain the electric charge of the photoconductor, and fulfills a function of transporting an electric charge injected from the charge generating layer upon receiving light. Resin binders include polycarbonates, polyesters, and metacrylate ester homopolymer and copolymers.

The ratio of the hydrazone compounds to resin binders is from 30 wt % to 70 wt %, preferably from 40 l wt % to 60 wt %. Chloroform, dichloromethane, benzene, toluene, methy ethyl ketone, tetrahydrofuran et al are used as a solvent.

The covering layer 7 has a function of receiving and retaining an electric charge generated by corona discharge in the dark and a capability of transmitting light to which the charge generating layer should respond. It is necessary that the covering layer transmits light upon exposure of the photoconductor and allows the light to reach the charge generating layer, and then undergoes the injection of an electric charge generated in the charge generating layer to neutralize and erases a surface electric charge. Materials usable in the covering layer include organic insulating film-forming materials such as polyesters and polyamides. Such organic materials may also be used in mixture with an inorganic material such as a glass resin or $SiO_2$, or a material for lowering electric resistance such as a metal or a metallic oxide. Materials usable in the covering layer are not limited to organic insulating materials for film-forming, and further include inorganic materials such as $SiO_2$, metals, and metallic oxides, which may be formed into a covering layer by an appropriate method such as vacuum evaporation and deposition, or sputtering. From the viewpoint of the aforementioned description, it is desirable that the material to be used in the covering layer be as transparent as possible in the wavelength range in which the charge generating substance attains maximum light absorption.

Although the thickness of the covering layer depends on the material or composition thereof, it can be arbitrarily set in so far as it does not produce any adverse effects including an increase in a˙ residual potential in continuous repeated use.

The hydrazone compounds can be used as a charge transporting substance is represented by the following general formula (I), (II) or (III):

The hydrazone compounds represented by the above-mentioned formula (I) used in the present invention can be easily synthesized by a customary method, that is, by condensation reacting the aldehydes represented by the following general formula (1) with the hydrazines represented by the following general formula (2) in an appropriate organic solvent such as ethanol in the presence of a catalyst such as an acid:

Wherein, A is a residual group selected from the group consisting of an aromatic residual group, a condensed polycyclic aromatic residual group, and a heterocyclic residual group, which groups may be or not may be substituted, $R_1$ is selected from the group or atom consisting of a hydrogen atom, a halogen atom, an alkyl group, an acyl group and a dialkylamino group.

Wherein, each of $R_2$ and $R_3$ is a group selected from the group consisting of an alkyl group, an aryl group, an alkenyl group, an aralkyl group and a thenyl group, which groups may be or not may be substituted.

Specific examples of the hydrazone compounds of the above-mentioned general formula (I) thus obtained include:

COMPOUND No I-1

No I-2

No I-3

No I-4

No I-5

No I-6

No I-7

No I-8

No I-9

No I-10

No I-11

No I-12

No I-13

No I-14

The hydrazone compounds represented by the above-mentioned formula (II) used in the present invention can be also easily synthesized by a customary method, that is, by condensation reacting the aldehydes represented by the following general formula (3) with the hydrazines represented by the foregoing general formula (2) in an appropriate organic solvent such as ethanol in the presence of a catalyst such as an acid:

(3)

Wherein, A is the same group as that of the general formula (1) as explained above.

Specific examples of the hydrazone compounds of the above-mentioned general formula (II) thus obtained include:

COMPOUND No II-1

No II-2

No II-3

No II-4

No II-5

No II-6

No II-7

-continued

No II-8

No II-9

No II-10

No II-11

No II-12

No II-13

No II-14

No II-15

-continued

No II-16

No II-17

No II-18

No II-19

No II-20

No II-21

In addition, the hydrazone compounds represented by the above-mentioned formula (III) used in the present invention can be also easily synthesized by a customary method, that is, by condensation reacting the aldehydes represented by the following general formula (4) with the hydrazines represented by the foregoing general formula (2) in an appropriate organic solvent such as ethanol in the presence of a catalyst such as an acid.

(4)

Wherein, $R_4$ is selected from the atom or group consisting of a hydrogen atom, a halogen atom and an alkyl group, and n is an integer of 1 or 2,

Specific examples of the hydrazone compounds of the above-mentioned general formula (III) thus obtained include:

COMPOUND No III-1

No III-2

No III-3

No III-4

No III-5

No III-6

No III-7

No III-8

-continued

No III-9

No III-10

No III-11

No III-12

No III-13

No III-14

The examples of the photoconductor according to the present invention will be explained.

EXAMPLE 1

50 parts by weight of metal-free phthalocyanine (H2Pc) of an X type and 100 parts by weight of the hydrazone compound No. I-1 mentioned above were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied on an aluminum-deposited polyester film (Al-PET) as an electroconductive substrate by means of the wire bar technique to form a photosensitive layer having a dry thickness of 15 μm. Thus, a photoconductor with a structure corresponding to that shown in FIG. 1 was produced.

EXAMPLE 2

80 parts by weight of the hydrazone compound No. I-2 as mentioned above and 100 parts by weight of polycarbonate resin (Panlite L-1225 (trademark), manufactured by Teizin Kasei Co., Ltd.) were solved in methylene chloride to prepare a coating liquid. The coating liquid thus obtained was applied on an aluminum-deposited polyester film substrate by means of wire bar method to form a charge transporting layer having a dry thickness of 15 μm. 50 parts by weight of titanyl phthalocyanine (TiOPc) pulverized with a ball mill for 150 hours was kneaded together with 50 parts by weight of a polyester resin (Vylon 200 (trademark)) and THF as a solvent with a mixer for 3 hours to prepare a coating liquid. The coating liquid was applied on the charge transporting layer by the wire bar method to form a charge generating layer having a dry thickness of 1 μm and then to form a covering layer thereon. Thus, a photoconductor with a structure corresponding to that shown in FIG. 3 was produced.

EXAMPLE 3

A photoconductor was produced in substantially the same manner as in Example 2 except that a squarylium compound represented by the following formula instead of TiOPc and the hydrazone compound No. I-3 as a charge transporting substance were used.

EXAMPLE 4

A photoconductor was produced by forming a photosensitive layer in substantially the same manner as in Example 2 except that the Chlorodiane Blue which is a bisazo pigment disclosed in, for example, Japanese Patent Application Laying-Open No. 37,543/1972 instead of TiOPc and the hydrazone compound No. I-4 as a charge transporting substance were used.

EXAMPLE 5

A photoconductor was produced in the same manner as in Example 1 except that the hydrazone compound No. III-1 as a charge transporting substance was used instead of the hydrazone compound No. I-1.

EXAMPLE 6

A photoconductor was produced in the same manner as in Example 2 except that the hydrazone compound No. III-2 as a charge transporting substance was used instead of the hydrazone compound NO. I-2.

EXAMPLE 7

A photoconductor was produced in the same manner as in Example 3 except that the hydrazone compound No. III-3 as a charge transporting substance was used instead of the hydrazone compound No. I-3.

EXAMPLE 8

A photoconductor was produced in the same manner as in Example 4 except that the hydrazone compound No. III-4 as a charge transporting substance was used instead of the hydrazone compound No. I-4.

The electrophotographic characteristics of the four photoconductors thus produced were measured by utilizing an electrostatic recording paper testing apparatus (Kawaguchi Denki Model SP-428).

The surface potential $V_s$ (volts) of each photoconductor is an initial surface potential which was measured when the surface of the photoconductor was positively charged in the dark by corona discharge at +6.0 kV for 100 seconds. After the discontinuation of the corona discharge, the photoconductor was allowed to stand in the dark for 2 seconds, after which the surface potential $V_d$ (volts) of the photoconductor was measured. Subsequently, the surface of the photoconductor was irradiated with white light at an illuminance of 2 luxes and the time (seconds) required for the irradiation to decrease the surface potential of the photoconductor to half of the $V_d$ was measured, then from which time and the illuminance the half decay exposure amount $E_{\frac{1}{2}}$ (lux·sec) was calculated. Also, the surface potential of the photoconductor after 10 seconds of irradiation thereof with white light at an illuminance of 2 luxes was measured as a residual potential $V_r$ (volts). As to the photoconductors of Example 1-3, and Examples 5-7, a high sensitivity could be expected for light with longer wavelengths. Hence, the electrophotographic characteristics thereof were also measured by using a monochromatic light with a wavelength of 780 nm. Specifically, the $V_s$ and the $V_d$ of each photoconductor were measured in the same manner as described above, and the half decay exposure amount ($\mu J/cm^2$) was found by irradiation of the photoconductor surface with a monochromatic light (wavelength: 780 nm) of 1 μW instead of white light, while the residual potential $V_r$ (volts) was measured after 10 seconds of irradiation of the photoconductor surface with the above-mentioned light. The results of the measurements are shown in Table 1.

TABLE 1

| Ex-ample No | White Light | | | Light with Wavelength of 780 nm | | |
|---|---|---|---|---|---|---|
| | $V_s$ (volt) | $V_r$ (volt) | $E_{\frac{1}{2}}$ (lux · sec) | $V_s$ (volt) | $V_r$ (volt) | $E_{\frac{1}{2}}$ ($\mu J/cm^2$) |
| 1 | 620 | 30 | 2.8 | 610 | 20 | 1.9 |
| 2 | 650 | 30 | 2.2 | 630 | 20 | 1.6 |
| 3 | 660 | 40 | 2.2 | 700 | 30 | 1.1 |
| 4 | 630 | 50 | 3.0 | — | — | — |
| 5 | 650 | 50 | 3.7 | 660 | 50 | 3.2 |
| 6 | 630 | 50 | 2.3 | 640 | 20 | 2.0 |
| 7 | 680 | 30 | 2.5 | 630 | 20 | 2.3 |
| 8 | 670 | 60 | 3.2 | — | — | — |

As can be seen in Table 1, the photoconductors of Examples 1 to 8 were not substantially different therebetween in the half decay exposure amounts and the residual potentials, and showed good surface potential characteristics. The photoconductors of Examples 1 to 3 and Examples 5 to 7, showed also excellent electrophotographic characteristics for light with a long wavelength of 780 nm. These photoconductors of Examples 1 to 3 and Examples 5 to 7 can be used for a semiconductor laser printer.

In addition, when the surface potentials of Examples 1 to 8 were repeatedly measured 100 times, the variations of the surface potentials before exposure were within 80V and the variations of the surface potentials after exposure were within 5V. The stabilities in repeated uses also showed excellent results.

EXAMPLE 9

Selenium was deposited on an aluminum plate having a thickness of 50 μm by means of vacuum evaporation to form a charge generating layer having a thickness of 1.5 μm. 100 parts by weight of hydrazone compound No. II-1 and 100 parts by weight of polycarbonate resin (PCZ 200 (trademark), manufactured by Mitsubishi Gas Kagaku Co., Ltd.) were solved in methylene chloride to form a coating liquid. The coating liquid was applied by means of the wire bar method on the charge generating layer to form a charge transporting layer having a dry thickness of 20 μm. Thus, a photoconductor with a structure corresponding to that shown in FIG. 2 was produced.

The electrophotographic characteristics of the photoconductor thus obtained were measured by utilizing testing apparatus SP-428 in the same manner as in Example 4 except that the potential of corona discharge was −6.0 kV. The Example 4 showed good results, namely $V_x = -620V$, $V_r = -40V$ and $E_{\frac{1}{2}} = 1.3$ lux·sec.

EXAMPLE 10

50 parts by weight of metal-free phthalocyanine of an X type pulverized with a ball mill for 150 hours and 50 parts by weight of vinyl chloride copolymer (MR-110 (trademark), manufactured by Nihon Zeon Co., Ltd.) were kneaded together with methylene chloride by use of a mixer for 3 hours to prepare a coating liquid. The coating liquid was applied on an aluminum substrate to form a charge generating layer having a thickness of about 1 μm. Subsequently, 100 parts by weight of the hydrazone compound No. II-2, 100 parts by weight of polycarbonate resin (Panlite L-1250 (trademark) and 0.1 part by weight of silicone oil were mixed with methylene chloride to prepare a coating liquid. The coating liquid was applied on the charge generating layer having a thickness of about 15 μm to form a charge transporting layer, thus a photoconductor was obtained.

The electrophotographic characteristics of the photoconductor thus obtained were measured in the same manner as in Example 9. The Example 10 showed good results, namely $V_x = -620V$ and $E_{\frac{1}{2}} = 1.1$ lux·second.

EXAMPLE 11

A photoconductor was produced in the same manner as in Example 10 except that a bisazo pigment of the following general formula was used instead of metal-free phthalocyanine of an X type and the hydrazone compound No. II-3 was used as a charge transporting substance:

The Example 11 showed, good results, namely $V_x = -600V$ and $E_{\frac{1}{2}} = 1.8$ lux·second.

EXAMPLE 12

A photoconductor was produced in the same manner as in Example 9 except that the hydrazone compound No. III-5 as a charge transporting substance was used instead of the hydrazone compound No. II-1.

The Example 12 showed good results, namely $V_s = -660V$, $V_r = -30V$ and $E_{\frac{1}{2}} = 2.9$ lux·second.

EXAMPLE 13

A photoconductor was produced in the same manner as in Example 10 except that the hydrazone compound No. III-6 as a charge transporting substance was used instead of the hydrazone compound No. II-2.

The Example 13 showed good results, namely $V_s = -660V$ and $E_{\frac{1}{2}} = 2.2$ lux·second.

EXAMPLE 14

A photoconductor was produced in the same manner as in Example 11 except that the hydrazone compound No. III-7 as a charge transporting substance was used instead of the hydrazone compound No. II-3.

The Example 14 showed good results, namely $V_s = -690V$ and $E_{\frac{1}{2}} = 3.1$ lux·second.

EXAMPLE 15

Photoconductors were produced in the same manner as in Example 4 except that the respective hydrazone compounds No. I-5 to No. I-14, No. II-4 to No. II-21 and No. III-8 to No. III-14 were used as a charge transporting substance.

The electrophotographic characteristics of these photoconductors were measured in the same manner as in Example 4. The measurement results of the half decay exposure amounts among them were shown in Table 2.

TABLE 2

| Compound No. | $E_{\frac{1}{2}}$ (lux · sec) |
|---|---|
| I-5 | 2.6 |
| I-6 | 2.1 |
| I-7 | 3.3 |
| I-8 | 3.1 |
| I-9 | 2.5 |
| I-10 | 2.1 |
| I-11 | 2.0 |
| I-12 | 3.8 |
| I-13 | 3.2 |
| I-14 | 1.9 |
| II-4 | 2.0 |
| II-5 | 2.6 |
| II-6 | 1.8 |
| II-7 | 1.9 |
| II-8 | 1.6 |
| II-9 | 2.5 |
| II-10 | 2.0 |
| II-11 | 2.8 |
| II-12 | 2.7 |
| II-13 | 3.2 |
| II-14 | 2.1 |
| II-15 | 2.7 |
| II-16 | 2.6 |
| II-17 | 2.5 |
| II-18 | 1.6 |
| II-19 | 2.2 |
| II-20 | 3.0 |
| II-21 | 2.1 |
| III-8 | 2.0 |
| III-9 | 1.9 |
| III-10 | 2.3 |
| III-11 | 1.5 |
| III-12 | 2.1 |
| III-13 | 2.1 |
| III-14 | 2.6 |

As can be seen in Table 2, the photoconductors using the respective hydrazone compounds No. I-5 to No. I-14, No. II-4 to No. III-21 and No. III-8 to No. III-14 as a charge transporting substance were satisfactory with respect to the half decay exposure amounts $E_{\frac{1}{2}}$.

According to the present invention, since a hydrazone compound represented by any one of the aforementioned general formula (I), (II) and (III) is used in a photosensitive layer formed on an electroconductive substrate, as a charge transporting substance, a photoconductor shows a high sensitivity and excellent characteristics in repeated use when adapted to either a positive charge mode or a negative charge mode. A suitable charge generating substance can be chosen so as to be adapted to the kind of exposure light source. By way of example, a phthalocyanine compound, a squarylium compound or a bisazo compound can be used as a charge generating substance to provide a photoconductor capable of being used in semiconductor laser printers. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A photoconductor for electrophotography, comprising:
   an electroconductive substrate; and
   a photosensitive layer formed on the electroconductive substrate and containing a charge generating substance and a charge transporting substance which is at least one hydrazone compound represented by general formula (I), (II) or (III);

wherein $A_1$ is a residual group selected from the group consisting of a thienyl residual group, a phenyl residual group, and a carbazole residual group, which groups may be substituted, $R_1$ is selected from the group consisting of a hydrogen atom, a halogen atom, an alkyl group, an acyl group, and a dialkylamino group, and each of $R_2$ and $R_3$ is a group selected from the group consisting of an alkyl group, an aryl group, an alkenyl group, an aralkyl group, and a thenyl group, which groups may be substituted, wherein $A_2$ is a residual group selected from the group consisting of a thienyl residual group, a phenyl residual group, and a naphthyl residual group, which groups may be substituted, and each of $R_2$ and $R_3$ is the same group as that of general formula (I), and wherein $R_4$ is selected from the group consisting of a hydrogen atom, a halogen atom, and an alkyl group, and each of $R_2$ and $R_3$ is the same group as that of general formula (I), and n is an integer and is 1 or 2.

2. The photoconductor as claimed in claim 1, wherein the photosensitive layer is a single layer comprised of a dispersion of the charge generating substance and the charge transporting substance in a binder resin.

3. The photoconductor as claimed in claim 1, wherein the photosensitive layer is a laminate comprised of a charge transporting layer comprising the charge transporting substance, and a charge generating layer comprising the charge generating substance.

4. The photoconductor as claimed in claim 3, wherein the charge generating layer is provided on the electroconductive substrate and the charge transporting layer is provided on the charge generating layer.

5. The photoconductor as claimed in claim 3, wherein the charge transporting layer is provided on the electroconductive substrate and the charge generating layer is provided on the charge transporting layer, and wherein the photosensitive layer further comprises a covering layer provided on the charge generating layer for protecting the charge generating layer.

* * * * *